United States Patent
Dague et al.

(10) Patent No.: US 10,835,655 B2
(45) Date of Patent: Nov. 17, 2020

(54) MOBILITY-ENHANCING BLOOD PUMP SYSTEM

(71) Applicant: TC1 LLC, St. Paul, MN (US)

(72) Inventors: Charles Dague, Chester, NH (US); Kevin Bourque, Reading, MA (US)

(73) Assignee: TC1 LLC, St. Paul, MN (US)

( * ) Notice: Subject to any disclaimer, the term of this patent is extended or adjusted under 35 U.S.C. 154(b) by 198 days.

(21) Appl. No.: 16/026,947

(22) Filed: Jul. 3, 2018

(65) Prior Publication Data

US 2018/0318483 A1 Nov. 8, 2018

Related U.S. Application Data

(63) Continuation of application No. 14/057,519, filed on Oct. 18, 2013, now Pat. No. 10,029,039, which is a
(Continued)

(51) Int. Cl.
*A61M 1/10* (2006.01)
*A61M 1/12* (2006.01)

(52) U.S. Cl.
CPC .......... *A61M 1/1086* (2013.01); *A61M 1/127* (2013.01); *A61M 1/101* (2013.01);
(Continued)

(58) Field of Classification Search
CPC .. A61M 1/1086; A61M 1/127; A61M 1/1008; A61M 1/122; A61M 1/101; A61M 1/12; A61M 2205/3334; A61M 2205/3523
See application file for complete search history.

(56) References Cited

U.S. PATENT DOCUMENTS 4,227,145 A 10/1980 Bonikowski et al.
4,888,011 A 12/1989 Kung, V et al.
(Continued)

FOREIGN PATENT DOCUMENTS

WO 9618358 A1 6/1996
WO 9805864 A1 2/1998
(Continued)

OTHER PUBLICATIONS

Dowling et al., "Initial Experience With the Abiocor Implantable Replacement Heart System", The Journal of Thoracic and Cardiovascular Surgery, vol. 127, Issue 1, 2004, pp. 131-141, 11 pages.
(Continued)

*Primary Examiner* — Lindsey G Wehrheim
(74) *Attorney, Agent, or Firm* — Kilpatrick Townsend & Stockton LLP

(57) ABSTRACT

A blood pump system includes a first implantable housing, an implantable blood pump independent from the first implantable housing, and a percutaneous extension. The first implantable housing includes a rechargeable power storage device. The implantable blood pump supplements the pumping function of a heart. The rechargeable power storage device supplies electrical power to the implantable blood pump. The percutaneous extension is coupled to the rechargeable power storage device and adapted to traverse the skin. The percutaneous extension is configured to releasably connect to an external power supply adapted to provide power for recharging or supplementing the rechargeable power storage device to power the implantable blood pump.

20 Claims, 8 Drawing Sheets

Related U.S. Application Data continuation of application No. 12/649,701, filed on Dec. 30, 2009, now Pat. No. 8,562,508.

(52) U.S. Cl.
CPC ............ *A61M 1/1008* (2014.02); *A61M 1/12* (2013.01); *A61M 1/122* (2014.02); *A61M 2205/3334* (2013.01); *A61M 2205/3523* (2013.01)

(56) References Cited

U.S. PATENT DOCUMENTS

| | | | |
|---|---|---|---|
| 4,969,864 A | | 11/1990 | Schwarzmann et al. |
| 5,099,089 A | | 3/1992 | Zan et al. |
| 5,250,894 A | | 10/1993 | Bridges et al. |
| 5,399,102 A | | 3/1995 | Devine |
| 5,569,156 A | * | 10/1996 | Mussivand ......... A61M 1/1063 600/16 |
| 5,613,935 A | | 3/1997 | Jarvik |
| 5,652,506 A | | 7/1997 | Sorenson et al. |
| 5,713,954 A | | 2/1998 | Rosenberg et al. |
| 5,725,357 A | | 3/1998 | Nakazeki et al. |
| 5,733,313 A | | 3/1998 | Barreras, Sr. et al. |
| 5,894,273 A | | 4/1999 | Meador et al. |
| 5,947,703 A | | 9/1999 | Nojiri et al. |
| 5,947,892 A | | 9/1999 | Benkowski et al. |
| 6,048,363 A | | 4/2000 | Nagyszalanczy et al. |
| 6,137,416 A | | 10/2000 | Meador |
| 6,146,325 A | | 11/2000 | Lewis et al. |
| 6,146,326 A | | 11/2000 | Pollack et al. |
| 6,149,683 A | * | 11/2000 | Lancisi ............... A61M 1/1017 623/3.1 |
| 6,176,822 B1 | * | 1/2001 | Nix ..................... A61M 1/1015 415/900 |
| 6,176,848 B1 | | 1/2001 | Rau et al. |
| 6,183,412 B1 | | 2/2001 | Benkowski et al. |
| 6,234,772 B1 | | 5/2001 | Wampler et al. |
| 6,264,601 B1 | | 7/2001 | Jassawalla et al. |
| 6,264,635 B1 | | 7/2001 | Wampler et al. |
| 6,370,427 B1 | * | 4/2002 | Alt ....................... A61N 1/0563 607/120 |
| 6,468,041 B2 | | 10/2002 | Ozaki |
| 6,575,717 B2 | | 6/2003 | Ozaki et al. |
| 6,589,030 B2 | | 7/2003 | Ozaki |
| 6,605,032 B2 | | 8/2003 | Benkowski et al. |
| 6,626,644 B2 | | 9/2003 | Ozaki |
| 6,688,861 B2 | | 2/2004 | Wampler |
| 6,707,200 B2 | | 3/2004 | Carroll et al. |
| 6,736,770 B2 | | 5/2004 | Leysieffer et al. |
| 6,817,836 B2 | | 11/2004 | Nose et al. |
| 6,949,066 B2 | * | 9/2005 | Bearnson ............. A61M 1/101 600/16 |
| 6,969,345 B2 | | 11/2005 | Jassawalla et al. |
| 7,138,776 B1 | | 11/2006 | Gauthier et al. |
| 7,150,711 B2 | | 12/2006 | Nusser et al. |
| 7,229,474 B2 | | 6/2007 | Hoffmann et al. |
| 7,239,098 B2 | | 7/2007 | Masino |
| 7,284,956 B2 | | 10/2007 | Nose et al. |
| 7,311,526 B2 | | 12/2007 | Rohrbach et al. |
| 7,462,019 B1 | | 12/2008 | Allarie et al. |
| 7,497,116 B2 | | 3/2009 | Miyakoshi et al. |
| 7,511,443 B2 | | 3/2009 | Townsend et al. |
| 7,563,225 B2 | | 7/2009 | Sugiura |
| 7,591,777 B2 | | 9/2009 | Larose |
| 7,645,225 B2 | | 1/2010 | Medvedev et al. |
| 7,699,588 B2 | | 4/2010 | Mendler |
| 7,854,631 B2 | | 12/2010 | Townsendl et al. |
| 7,861,582 B2 | | 1/2011 | Miyakoshi et al. |
| 7,887,479 B2 | | 2/2011 | Larose et al. |
| 7,951,062 B2 | | 5/2011 | Morello |
| 7,976,271 B2 | | 7/2011 | Larose et al. |
| 8,157,720 B2 | | 4/2012 | Marseille et al. |
| 8,272,585 B2 | | 9/2012 | Abramson et al. |
| 8,303,482 B2 | | 11/2012 | Schima et al. |
| 8,323,174 B2 | | 12/2012 | Jeevanandam et al. |
| 8,382,830 B2 | | 2/2013 | Maher et al. |
| 8,506,470 B2 | | 8/2013 | Larose et al. |
| 8,517,699 B2 | | 8/2013 | Horvath |
| 8,556,795 B2 | | 10/2013 | Bolyard et al. |
| 8,562,508 B2 | | 10/2013 | Dague et al. |
| 8,597,350 B2 | | 12/2013 | Rudser et al. |
| 8,620,447 B2 | | 12/2013 | D'Ambrosio et al. |
| 8,764,621 B2 | | 7/2014 | Badstibner et al. |
| 8,870,739 B2 | | 10/2014 | Larose et al. |
| 8,882,477 B2 | | 11/2014 | Fritz, IV et al. |
| 8,956,275 B2 | | 2/2015 | Bolyard et al. |
| 10,029,039 B2 | | 7/2018 | Dague et al. |
| 2003/0114899 A1 | | 6/2003 | Woods et al. |
| 2004/0082868 A1 | | 4/2004 | Campbell et al. |
| 2005/0071001 A1 | | 3/2005 | Jarvik |
| 2007/0142696 A1 | * | 6/2007 | Crosby .................... A61N 1/36 600/16 |
| 2007/0212929 A1 | | 9/2007 | Huang et al. |
| 2008/0319544 A1 | | 12/2008 | Yaegashi |
| 2009/0088723 A1 | | 4/2009 | Khosravi et al. |
| 2010/0130809 A1 | | 5/2010 | Morello |
| 2010/0241223 A1 | | 9/2010 | Lee et al. |
| 2010/0256440 A1 | | 10/2010 | Maher et al. |
| 2010/0305692 A1 | * | 12/2010 | Thomas ................ A61M 1/127 623/3.1 |
| 2010/0327687 A1 | | 12/2010 | Iannello et al. |
| 2011/0071336 A1 | | 3/2011 | Yomtov et al. |
| 2011/0071337 A1 | | 3/2011 | Thompson et al. |
| 2011/0160516 A1 | | 6/2011 | Dague et al. |
| 2011/0237863 A1 | | 9/2011 | Ricci et al. |
| 2011/0313237 A1 | | 12/2011 | Miyakoshi et al. |
| 2011/0313517 A1 | * | 12/2011 | Reichenbach ...... A61M 1/1086 623/3.11 |
| 2012/0226097 A1 | | 9/2012 | Smith et al. |
| 2012/0245681 A1 | | 9/2012 | Casas et al. |
| 2013/0331934 A1 | | 12/2013 | Kabir et al. |
| 2014/0073838 A1 | | 3/2014 | Dague et al. |
| 2014/0100413 A1 | | 4/2014 | Casas et al. |
| 2014/0194985 A1 | | 7/2014 | Vadala, Jr. |
| 2014/0275723 A1 | | 9/2014 | Fritz et al. |
| 2014/0275727 A1 | | 9/2014 | Bonde et al. |
| 2014/0303426 A1 | | 10/2014 | Kerkhoffs et al. |
| 2014/0357937 A1 | | 12/2014 | Reyes et al. |
| 2015/0051438 A1 | | 2/2015 | Taskin |

FOREIGN PATENT DOCUMENTS

| | | |
|---|---|---|
| WO | 9917819 A1 | 4/1999 |
| WO | 2005075017 A1 | 8/2005 |
| WO | 2007006080 A1 | 1/2007 |
| WO | 2007090050 A2 | 8/2007 |
| WO | 2010138742 A1 | 12/2010 |

OTHER PUBLICATIONS

Dowling et al., "The Abiocor Implantable Replacement Heart", The Annals of Thoracic Surgery, vol. 75, Issue 6, 2003, pp. S93-S99, 7 pages.

Pae et al., "Does Total Implantability Reduce Infection With the Use of a Left Ventricular Assist Device? The Lionheart Experience in Europe.", The Journal of Heart and Lung Transplantation, vol. 26, Issue 3, 2007, pp. 219-229, 11 pages.

\* cited by examiner

MOBILITY-ENHANCING BLOOD PUMP SYSTEM

CROSS-REFERENCES TO RELATED APPLICATIONS

The present application is a Continuation of U.S. application Ser. No. 14/057,519 filed Oct. 18, 2013 (Allowed); which is a Continuation of U.S. application Ser. No. 12/649,701 filed Dec. 30, 2009 (now U.S. Pat. No. 8,562,508; the full disclosures of which are incorporated herein by reference in their entirety for all purposes.

TECHNICAL FIELD

This document relates to implanted medical pump systems, such as ventricular assist pumps, and components, such as controllers and batteries associated with the pump systems.

BACKGROUND

The human heart is a complex and critical pump. Due to various pathologies, the heart can become dysfunctional, acutely or chronically. When damage to the heart becomes sufficiently symptomatic by clinical measures, the heart may be diagnosed as cardiomyopathic, a form of heart failure. In such a situation, a doctor can recommend mechanical assistance among the few therapeutic options that include pharmacologic therapy and heart transplantation. Where an afflicted person is scheduled to receive a transplant, mechanical assistance may be a choice of therapy until a donor heart becomes available.

Blood pumps are commonly used to provide mechanical augmentation to the pumping performed by the left and/or right ventricles of the heart. Ventricular assistance may be provided by an implantable pump that is connected in parallel with the person's heart and may be regulated by a controller. The controller and the pump use a power source, such as one or more external batteries or electrical connection to a wall socket. A blood pump generally uses about 1-10 W of power. Connection to a sufficient power source to operate the pump and controller can make mobility difficult, which can reduce the quality of life for a patient.

SUMMARY

A blood pump system is described that includes a first implantable housing, an implantable blood pump independent from the first implantable housing, and a percutaneous extension. The first implantable housing includes a rechargeable power storage device. The implantable blood pump supplements the pumping function of a heart. The rechargeable power storage device supplies electrical power to the implantable blood pump. The percutaneous extension is coupled to the rechargeable power storage device and adapted to traverse the skin. The percutaneous extension is configured to releasably connect to an external power supply adapted to provide power for recharging or supplementing the rechargeable power storage device to power the implantable blood pump.

The first implantable housing can have a volume that ranges from about 1 in$^3$ to about 20 in$^3$. For example, the first implantable housing can have a volume that ranges from 7 in$^3$ to 13 in$^3$. In some embodiments, the implantable housing has a volume of about 10 in$^3$. By having the first implantable housing independent from the blood pump, the housing can be sized to include a larger power storage device having a larger power storage capacity, which can extend the length of time that the blood pump can be operated with power supplied from the power storage device. In some embodiments, the rechargeable power storage device can supply electrical power for normal operation of the blood pump for a period of time of at least 30 minutes. In some embodiments, the rechargeable power storage device can supply electrical power for normal operation of the blood pump for a period of time of at least 2 hours. In some embodiments, the rechargeable power storage device can supply electrical power for normal operation of the blood pump for a period of time of at least 3.5 hours. In some embodiments, the rechargeable power storage device can supply electrical power for normal operation of the blood pump for a period of time of about 5 hours. In some embodiments, the rechargeable power storage device can be recharged from a functionally depleted state to a fully charged state in less than about 1 hour.

The first implantable housing can further include an implanted telemetering device. For example, the system further includes an external monitoring device that includes an external telemetering device that communicates wirelessly with the implanted telemetering device. In some embodiments, one of an internal system controller and an external monitoring device is adapted to notify the patient that an amount of electrical charge remaining in the rechargeable power storage device is less than a minimum threshold (e.g., by vibrating, by light, by sound). The minimum threshold can be the amount of electrical charge normally used for normal operation of the blood pump, e.g. 30 minutes. In some embodiments, the first implantable housing is adapted to vibrate to notify the patient that the amount of electrical charge remaining is less than the minimum threshold.

The system can include two rechargeable power storage devices that supply electrical power to the blood pump. The second rechargeable power storage device can be within the first implantable housing or, in other embodiments, within a second implantable housing. In some embodiments, a second implantable housing encloses the blood pump and includes pump controller circuitry that controls the operation of the blood pump. The system can include a rechargeable battery electrically connected to the pump controller circuit for supplying electrical power to the pump controller circuit.

The percutaneous extension can include a plurality of wires that traverse the skin and carry electrical current to recharge or supply power to the rechargeable power storage unit. In some embodiments, the percutaneous extension has a cross-sectional area that is less than about 0.1 in$^2$. The percutaneous extension can also include an electrical connector coupled to the plurality of wires and adapted to couple to a portion of the external power supply. In some embodiments, the percutaneous extension includes at most four wires. In other embodiments, the percutaneous extension includes more than four wires. For example, the percutaneous extension can include two redundant sets of two wires, wherein each redundant set of wires can carry electrical current to recharge the rechargeable power storage unit.

The percutaneous extension can include a fluid-resistant sheath that is coupled to the electrical connector and that surrounds the plurality of wires along substantially the length of the plurality of wires. In some embodiments, the percutaneous extension can include a fluid resistant cap adapted to be removably coupled to the electrical connector for protecting the interior of the electrical connector from contact with external fluids when the electrical connector is not coupled to a portion of the external power supply. In some embodiments, the system includes an internal power sensing feature that detects an amount of power remaining in the rechargeable power storage device and a cap or an external end of the percutaneous extension is adapted to emit a light when the power sensing feature determines that the amount of power remaining in the rechargeable power storage device is less than a minimum threshold.

The system can include an internal system controller that controls the operation of the blood pump. In some embodiment, an internal system controller can be included in the first implantable housing.

The external power supply can be, for example, a battery or a converted AC source. The external power supply can be adapted to supply electrical power for the normal operation of the blood pump.

The blood pump can be a ventricular assist device (e.g., an LVAD).

The system can be implanted in a user and used for mechanical assistance to the user's heart and/or to replace the heart. The user can connect the percutaneous lead to an external power supply to supply power to the blood pump or to charge the rechargeable power storage device. The user can also disconnect the percutaneous lead from the external power supply for a period of at least 30 minutes, during which the rechargeable power storage device supplies power to the heart pump. The user can then reconnect the percutaneous lead to the external power supply to recharge the power storage device or to supply power to the blood pump.

In another aspect, the system includes an implantable blood pump that supplements the pumping function of a heart, an internal system controller that controls the operation of the implantable blood pump, a rechargeable power storage device that supplies electrical power to the implantable blood pump and is adapted to supply electrical power for the normal operation of the implantable blood pump for a period of time of at least 30 minutes, and a percutaneous extension coupled to the rechargeable power storage device adapted to traverse the skin and to releasably connect to an external power supply to provide power to supplement or recharge the rechargeable power storage device. In some embodiments, the rechargeable power storage device has a volume that is greater than about 7 in$^3$.

In another aspect, the system includes a first implantable housing including an internal system controller and a rechargeable power storage device, a blood pump that supplements the pumping function of a heart, and a percutaneous extension. The first implantable housing is coupled to the blood pump via one or more electrical wires, and the rechargeable power storage device supplies electrical power to the blood pump for the normal operation of the blood pump for a period of not less than 30 minutes. The system also includes an external device that wirelessly communicates with the internal system controller. The percutaneous extension is adapted to traverse the skin and to releasably connect to an external power supply to provide power to the rechargeable power storage device. The percutaneous extension includes two redundant sets of two wires. Each redundant set of wires is adapted to carry electrical current to recharge the rechargeable power storage unit. The percutaneous extension also includes an electrical connector coupled to the plurality of wires and adapted to couple to a portion of the external power supply. The percutaneous extension also includes a water-resistant sheath that is coupled to the electrical connector and that surrounds the plurality of wires along substantially the length of the plurality of wires. In some embodiments, the percutaneous extension has a cross-sectional area that is less than about 0.1 in$^2$. In some embodiments, the first implantable housing has a volume that ranges from about 1 in$^3$ to about 20 in$^3$.

The blood pump system can be configured with features to decrease the possibility of infection. The percutaneous lead can be configured to have a smaller diameter, thus lowering the possibility of infection around the skin opening through which the percutaneous lead passes. With a percutaneous lead that can be used for recharging the internal power storage devices, other more cumbersome power transfer methods, such as transcutaneous power transfer, can be avoided. Since transcutaneous power systems require the formation of large surgical pockets within the patient to hold the associated equipment, such as energy transferring coils, systems that do not include a transcutaneous power transfer system reduce the possibility of infection in and surrounding the pockets. Furthermore, systems that incorporate a percutaneous lead for power transfer advantageously reduce power losses during transfer and eliminate tissue heating, when compared to systems incorporating transcutaneous power transfer.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

An exemplary hybrid blood pump system generally includes a blood pump, at least one internal rechargeable power storage device, and a percutaneous lead. The hybrid blood pump system is configured to enhance the freedom and mobility of the user by allowing for normal function of the blood pump when the user is disconnected from an external power source. The internal rechargeable power storage device can store sufficient power to provide for the normal operation of the blood pump for an extended period of time (e.g., at least about 30 minutes and ideally at least 2 hours). The percutaneous lead allows for the percutaneous transfer of power from an external source to normally operate the blood pump and to recharge the internal power storage device. The hybrid system, which can run on power supplied by either an internal rechargeable power storage device, or by a direct connection with an external power source via the percutaneous lead, provides a system that allows for increased mobility while avoiding problems associated with fully implanted systems that transfer power transcutaneously. Exemplary hybrid systems are described below in connection with the attached figures.

Figure 1:
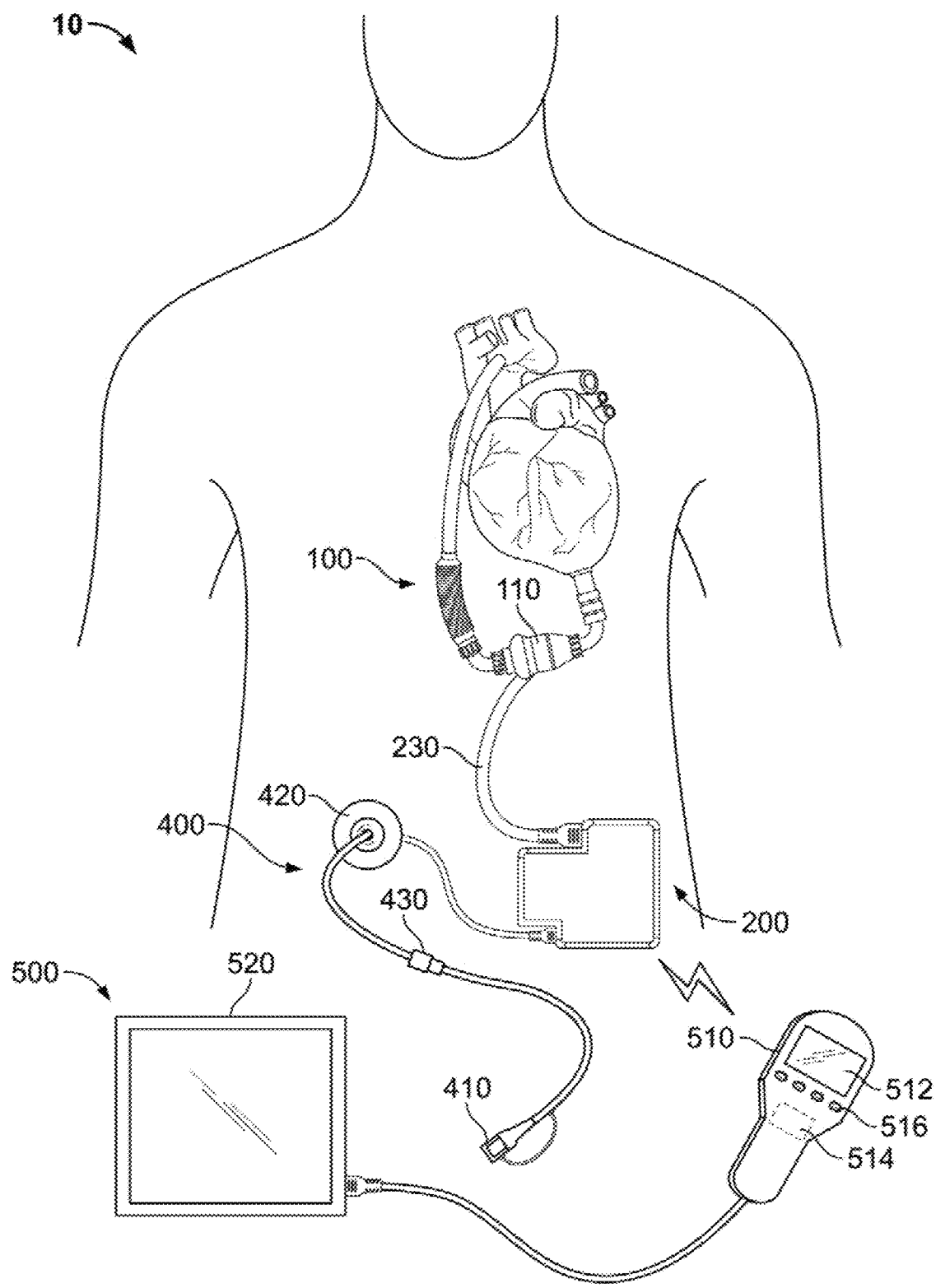
FIG. 1 is a front view depicting one embodiment of a mobility-enhancing hybrid ventricular assist system implanted in a patient and an external communication device.
Figure 2:
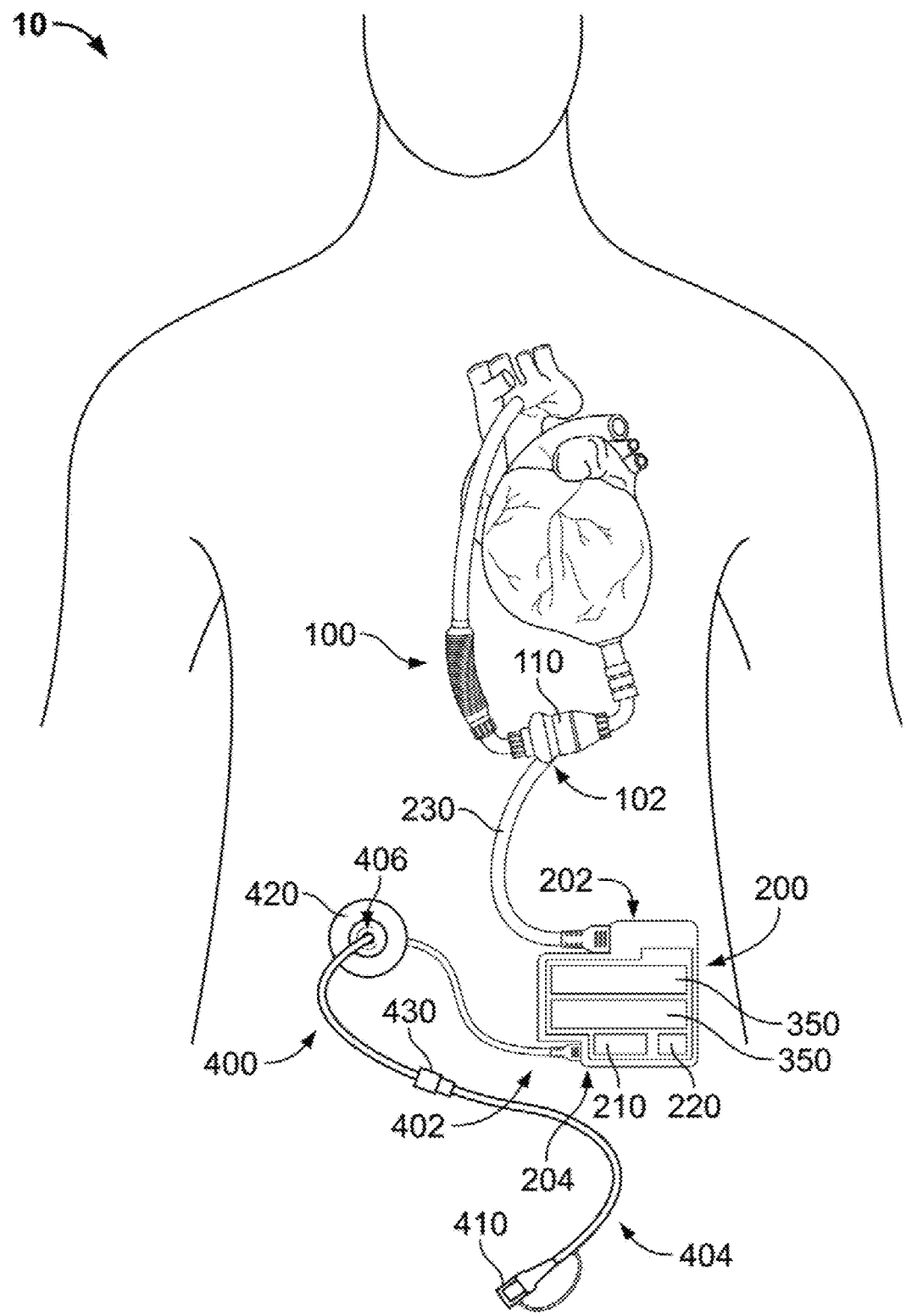
FIG. 2 is a front view depicting one embodiment of a mobility-enhancing hybrid ventricular assist system implanted in a patient, the hybrid system including a blood pump, a controller, rechargeable power storage devices, and a compact percutaneous lead.

FIG. 1 is a front view depicting an example of a mobility-enhancing hybrid ventricular assist system 10 including an internal blood pump assembly 100, an internal controller assembly 200 connected to the blood pump assembly via an electrical conduit 230, internal rechargeable power storage device(s) 350 contained within the controller assembly 200 (see FIG. 2), and a percutaneous lead 400 connected to the controller assembly 200 and exiting the body. The power storage device(s) 350 include one or more "smart" lithium-chemistry batteries that are readily rechargeable. An external monitoring device 500 can perform wireless 2-way communication with the internal components of the hybrid system 10, for example, via wireless telemetry device 220 (see FIG. 2). FIG. 2 is a close-up of the system of FIG. 1, not showing the external monitoring device 500 but showing exemplary internal components of the controller assembly 200. As depicted in FIG. 1, the internal pump assembly 100 can also include an implantable blood pump 110 fluidly connected to an internal chamber of a heart and circulatory system, and a programming wand 510 included in the external monitoring device 500 for communication with the controller assembly 200. The programming wand can include a built-in display 512 for displaying menus, data, and the like, and a external wireless telemetry device 514 for communicating with the internal telemetry device 220 and one or more user-selectable buttons 516 (e.g., four buttons in this embodiment).

Blood Pump

The blood pump 110 can be a ventricular assist device (VAD). A VAD is a mechanical circulatory device that is used to partially or completely replace the function of a failing heart. Some VADs are intended for short term use, typically for patients recovering from heart attacks or heart surgery, while others are intended for long term use (e.g., months, years, and the remainder of a user's life), typically for patients suffering from congestive heart failure. VADs are designed to assist either the right (RVAD) or left (LVAD) ventricle, or both at once (BiVAD). VADs can be designed with an axial flow or centrifugal flow configuration. The former can be configured with an impeller suspended by journal bearing such as a ball and cup, or by magnetic or hydrodynamic forces. The latter can be configured with an impeller suspended by at least magnetic forces, hydrodynamic forces, or a combination of both. In other embodiments, the blood pump can be an artificial heart, which is designed to completely take over cardiac function and may require the removal of a patient's heart. It should be appreciated that the technical features disclosed herein apply equally to any variation of the blood pump as described in this disclosure.

Figure 7:
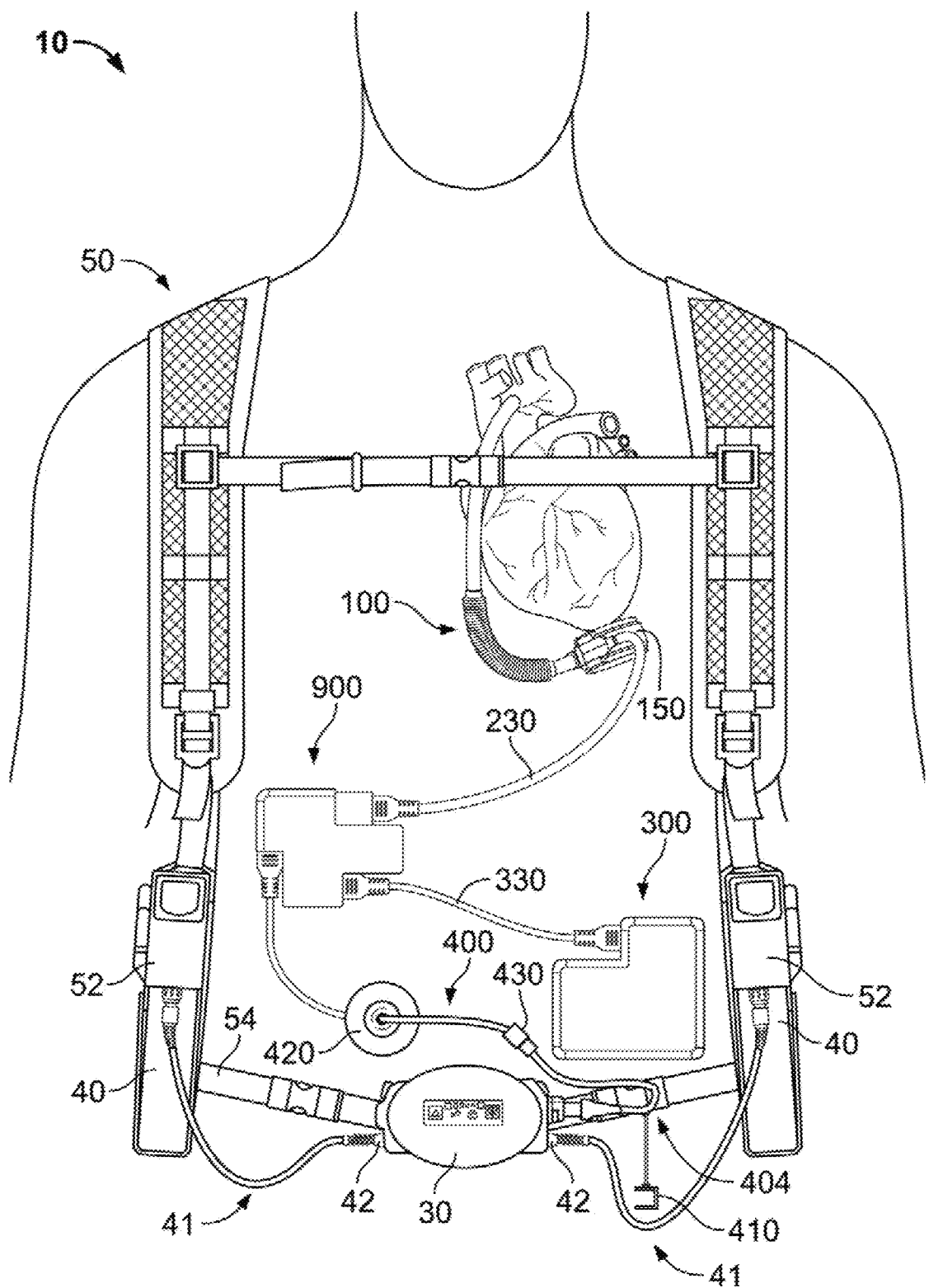
FIG. 7 depicts a front view of one embodiment of a mobility-enhancing hybrid ventricular assist system implanted in a patient with the hybrid system connected to an external controller and external batteries contained in a carrier system.
Figure 8:
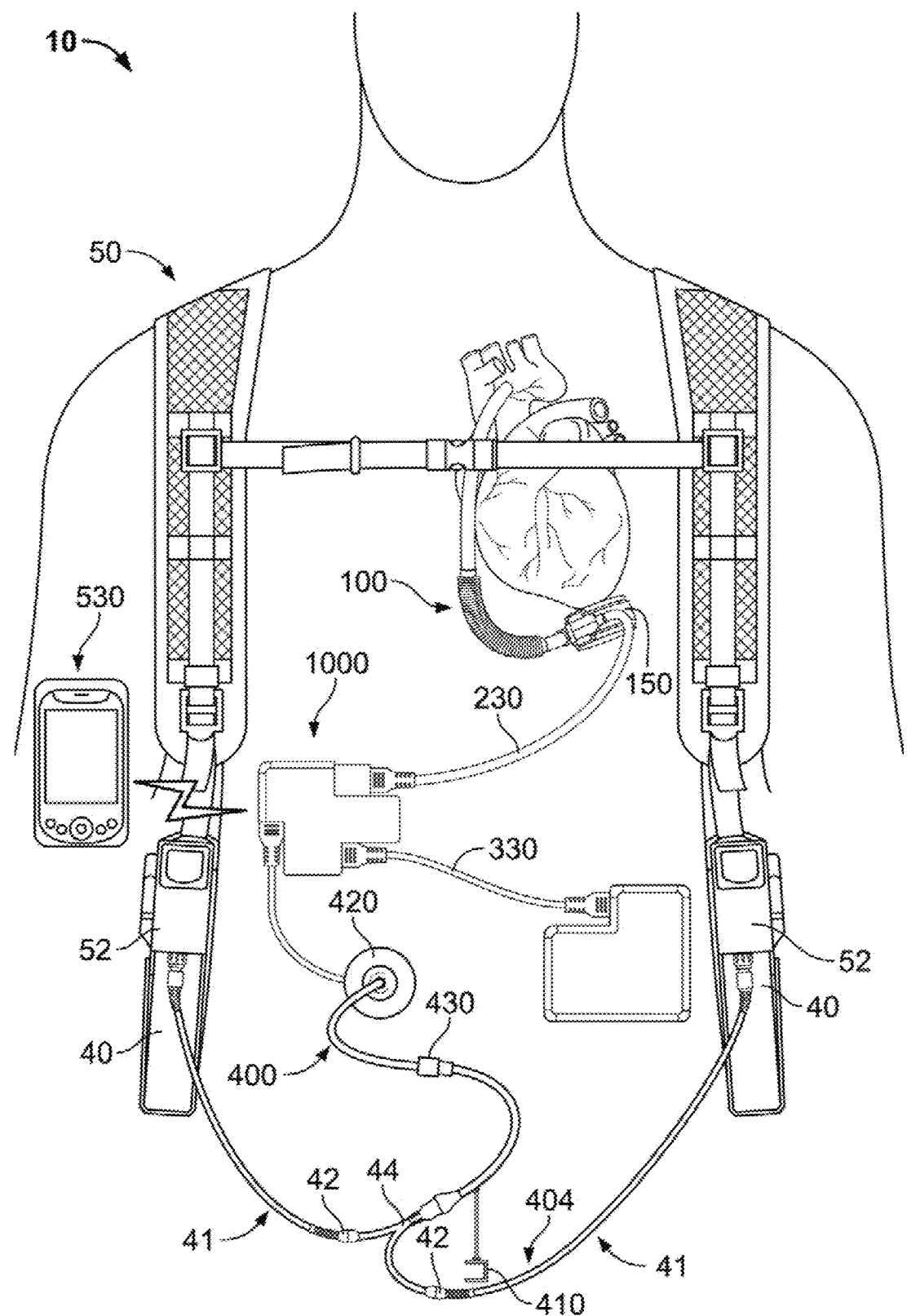
FIG. 8 depicts a front view of one embodiment of a mobility-enhancing hybrid ventricular assist system implanted in a patient with the hybrid system connected to external batteries contained in a carrier system and in wireless communication with an external interface.

As depicted in FIG. 1, a hybrid ventricular assist system 10 can include the internal pump assembly 100 connected in parallel with the left ventricle of a heart such that the pump assembly 100 can mechanically augment the pumping of blood performed by the left ventricle. In particular, FIGS. 1 and 2 depict the internal pump assembly 100 including the blood pump 110, such as the HeartMate® II LVAD, a product of the Thoratec® Corporation of Pleasanton, Calif., while FIGS. 7 and 8 depict the pump assembly 100 that includes a different embodiment of an LVAD. For example, the pump assembly 100 can be installed to temporarily provide mechanical assistance while an individual waits for a transplant. In other examples, the pump assembly 100 can be implanted to reduce the stress on a person's heart, allowing it to heal and regain normal function, and later be removed. In yet other examples, the pump assembly 100 can be implanted as a substantially permanent option.

The blood pump can include internal pump control circuitry. Internal pump control circuitry can also be included in a separate housing (e.g., with internal rechargeable power storage device). Internal pump control circuitry functions to make the blood pump pump when power is supplied to the blood pump and is distinct from a controller that may alter the pumping operation, alter how power is being supplied to the blood pump and/or perform other functions for the system, such as detecting whether the system is being provided with power from an external power source and detecting whether the internal rechargeable power source needs to be recharged from the external power source.

Internal Power Storage Device(s)

Figure 3A:
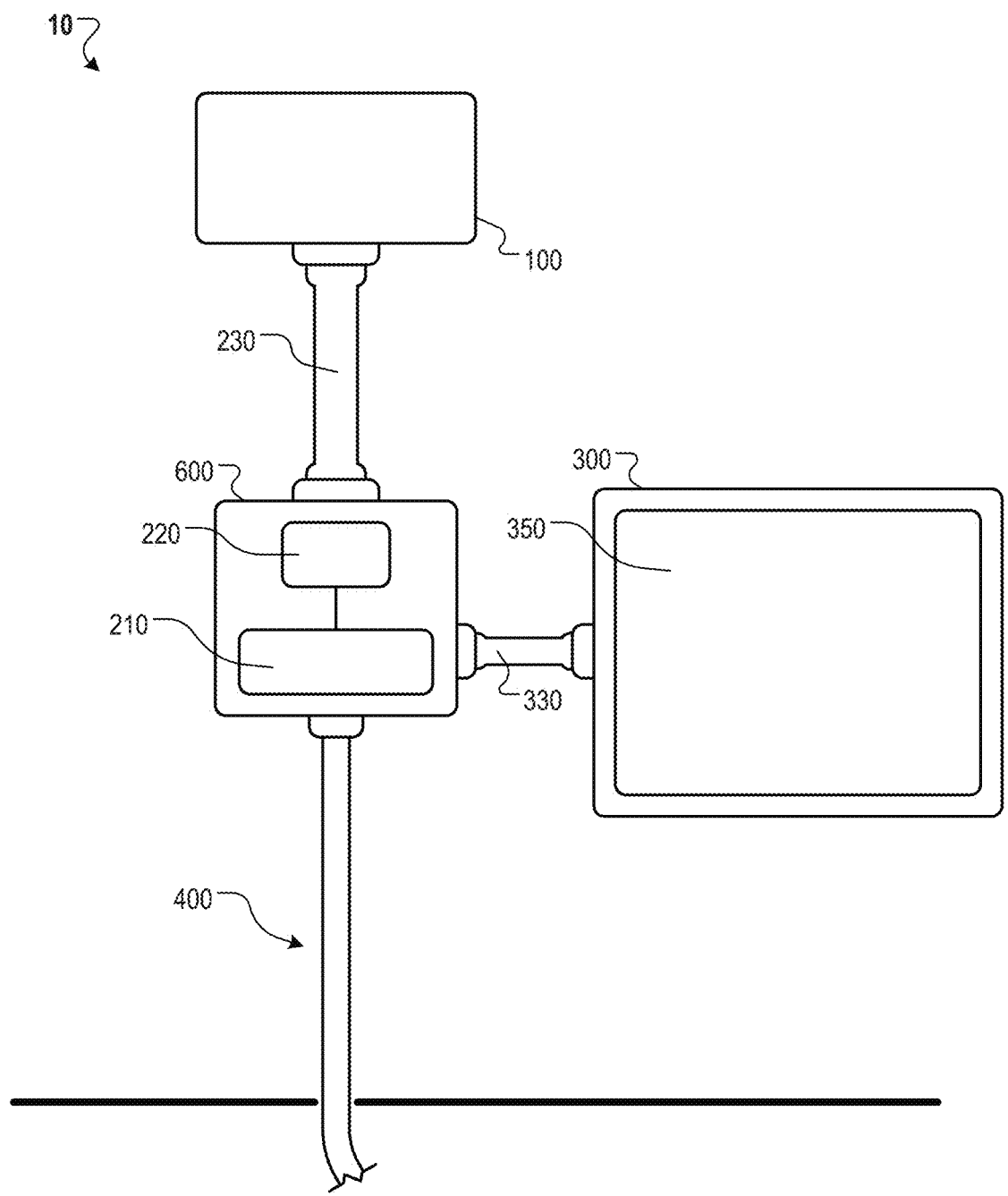
FIG. 3A is schematic representation of one embodiment of a mobility-enhancing hybrid ventricular assist system including a controller assembly and a power storage assembly, each separate from the blood pump.
Figure 3B:
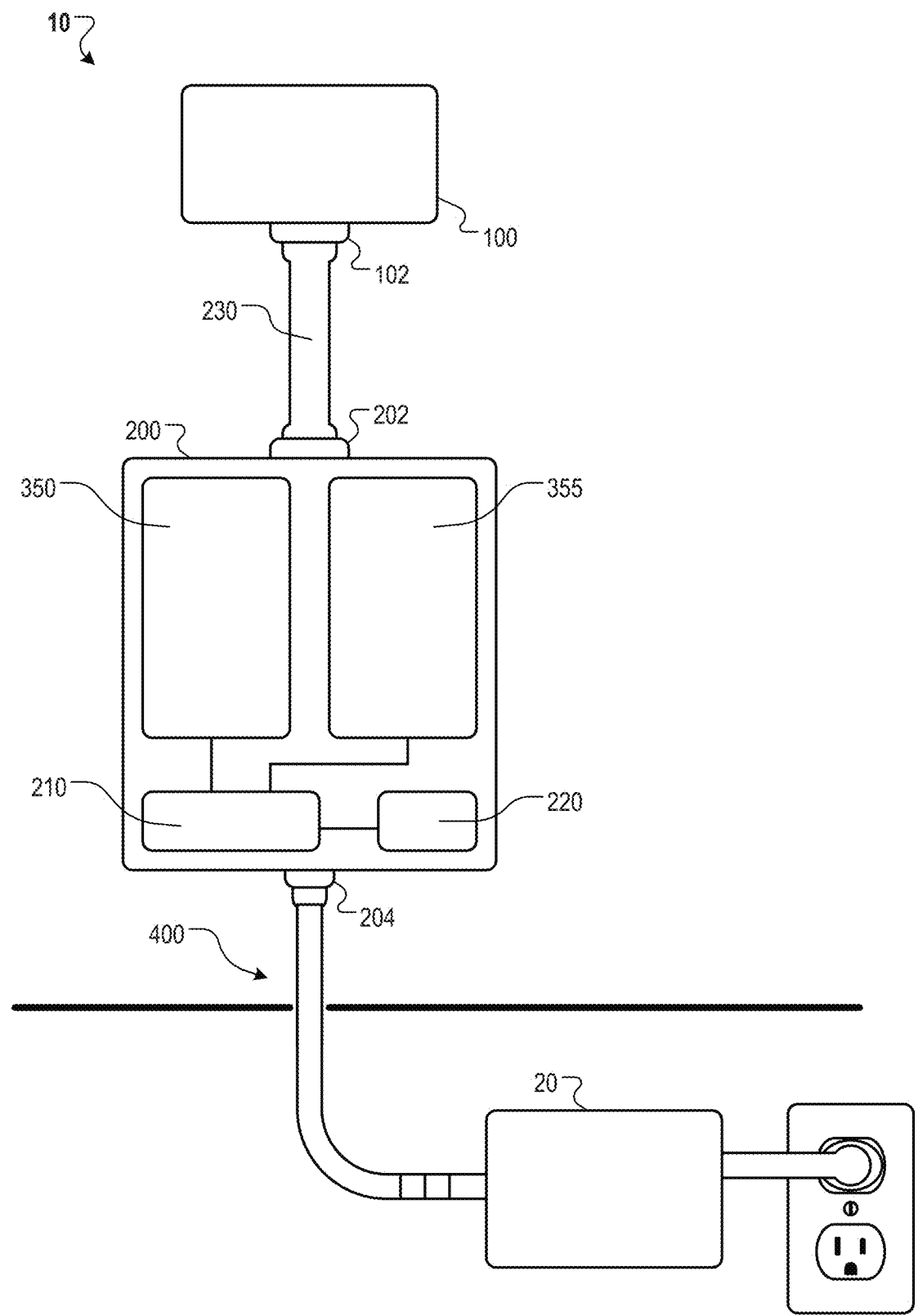
FIG. 3B is schematic representation of another embodiment of a mobility-enhancing hybrid ventricular assist system connected to an external power source.

One or more power storage devices 350 can be included in a single housing. In some embodiments, this single housing also includes a controller device 210. As depicted in FIGS. 1, 2, and 3B, a controller device 210 and the power storage device(s) 350 can be within the single controller assembly 200. As depicted in FIG. 2, a controller assembly can include two (or more) power storage devices 350. In other embodiments, the controller assembly can include a single power storage device, or any number of power storage devices. In still other embodiments, such as depicted in FIGS. 3A, 7, and 8, the hybrid system 10 can include one or more housings, separate from the controller assembly, each containing one or more power storage devices.

As depicted in the FIGS. 1 and 2, the power storage device(s) 350 can be implanted in a location separate from the blood pump assembly 100, for example, in the thorax or the abdomen of a patient. In particular examples, the housing can be implanted in the abdominal quartet, below the thorax, within the mussel layers. In other embodiments, the power storage device(s) 350 can be implanted in other body locations, such as within the leg of a patient. A housing containing the power storage device(s) 350 can be positioned and shaped to maximize the dissipation of heat from the power storage device(s) 350. For example, the housing can be positioned to maximize the amount of blood circulating around the housing. Accordingly, it can be advantageous to implant the housing containing the power storage device(s) 350 at or near the core of the patient. Implanting the power storage device(s) 350 within a housing in a location separate from the blood pump assembly 100 can allow for the use of a larger power source than can normally be accommodated within the blood pump assembly. It can be desirable to limit the volume of devices implanted adjacent to the heart. As such, a battery implanted inside or in close proximity to a blood pump assembly 100 is limited in size, and thus electrical capacity. To allow for a longer period of time in which the user is not connected to an external power source, the power storage device(s) can be advantageously included in a location separate from the blood pump assembly. Locations such as the abdomen may be able to accept larger implanted devices, and thus allow for larger power storage device(s), which can be used to increase the period of time that the internal blood pump can function normally without being coupled to an external power source. Moreover, having the power storage device(s) 350 in a location separate from the blood pump assembly 100 can reduce the probability of heat from the internal power storage device(s) damaging the heart and/or tissue adjacent the heart. Furthermore, a location of the power storage device separate from the blood pump assembly allows for outpatient replacement of the power storage device, if necessary. Thus, a location can also be selected in accordance with the level of ease in which the power storage device can be replaced.

The total volume of the power storage device(s) 350 can be 1 in$^3$ or greater. In some embodiments, the total volume of a housing including the power storage device(s) is between about 1 in$^3$ and about 20 in$^3$. In some embodiments, the power storage device(s) are designed with various options based on size and run time, including but not limited to providing greater than 30 minutes of blood pump normal operation, greater than 1 hour of blood pump normal operation, greater than 2 hours of blood pump normal operation, and greater than 3.5 hours of blood pump normal operation. The housing can, in preferred embodiments, have a volume of between 5 in$^3$ and 13 in$^3$ (e.g., about 10 in$^3$). The total volume of a housing would also depend on the material used and the battery technology. Generally, there is a tradeoff between size and run time. For instance, the larger the rechargeable power source the larger the charge storage capacity and thus the longer the run time. However, there is also a higher risk of infection. On the other hand, the smaller housing containing a smaller rechargeable power source would have a smaller charge storage capacity, a shorter run time, but a lower risk of infection.

The housing, like most implanted components, can be hermetically sealed. The housing can be made of commercially available inert materials including both biocompatible metals, biocompatible polymers, and biocompatible ceramics, such as stainless steel, titanium and titanium alloys (e.g., Ti-6Al-4V grade 5 titanium), cobalt-chromium alloys, polyethylene (e.g., UHMWPE), PEEK polymers, and combinations thereof. The housing material can also be selected for its ability to dissipate heat as well as its ability to provide an electrical and/or magnetic shield should it be used to house an internal controller. The housing can be substantially flat. For example, the housing can have a thickness of about 0.3 to 1 inch, a width of about 1.5 to 3.5 inches, and a length of about 3 to 6 inches. In some embodiments, the housing has dimensions approximating the dimensions of a standard cigarette pack (about 2.6 inches×about 4.6 inches×about 0.6 inches). In some embodiments, the housing can have a slightly curved configuration bent to confirm to the contours of a human abdomen, similar to a whisky flask. The housing can also have rounded corners. This can allow a user to have increased freedom of movement because batteries of this volume can be used to provide power for normal pump operation for extended periods of time without the use of an external power supply. A flat configuration can allow for a more superficial placement and replacement, if necessary. A flat configuration can also facilitate the dissipation of heat. The housing can also have rounded corners and other features to reduce injury to surrounding tissue. An outer surface of the housing can having a coating or other features that reduce the instances of pocket infection.

As the pump is directly connected to the heart, the size of the implant adjacent to the heart should be minimized. As the size of the implant increases, so does the risk of a pocket infection. If the pump pocket becomes infected, the infection could enter the blood stream causing sepsis, which can be extremely hazardous to an already immuno-compromised patient. An implant of minimal size adjacent to the heart can allow for placement of the device entirely within the thorax which may simplify the surgery and allow for a shorter recovery time.

The power storage device(s) 350 can be one or more rechargeable batteries. For example, the power storage device(s) 350 can be one or more lithium ion batteries. In other embodiments, the power storage device(s) 350 can be one or more lithium polymer batteries. In other examples, the power storage device(s) 350 may comprise a capacitor device capable of being recharged over time and discharging power sufficient for normal operation of the system 10. Still, fuel cell technology using hydrogen as an energy storage vehicle may provide a viable option, using electricity provided by an external power source to electrolyze water within the body to generate additional hydrogen. Still, other high density power storage devices may be developed in the future and can be used in as the power storage device(s) 350 as described herein.

Because some batteries may become non-rechargeable if fully depleted, some batteries, such as "smart" lithium-polymer batteries, can include internal circuitry that prevents the batteries from becoming fully depleted. As such, if the charge level within such a battery falls below a predetermined level, this internal circuitry can cause the battery to stop delivering power to avoid irreversibly damaging the battery. Accordingly, if the charge within a battery falls below this predetermined level, the battery is functionally depleted. As an alternative, the controller device 210 can determine whether the energy remaining in a particular power storage device 350 has fallen below a predetermined threshold and can stop transferring power from a power storage device 350 if the remaining energy falls below that predetermined threshold. Still, another possibility is to have the controller device 210 send a warning signal when the power capacity drops below a certain level and into a range where operation of the pump is still possible, but before it is considered functionally depleted.

When connected to an external power source, the internal power storage devices 350 can be recharged using energy from the external power source. Charge time can depend on the size of the battery and the charge rate limitations for heat dissipation in the charge electronics and the heat dissipation in the percutaneous lead. For example, power storage devices can be recharged in 50% to 400% of the discharge time. In some embodiments, the internal power storage devices can be recharged from a functionally depleted state to having a full charge in less than 30 minutes.

Percutaneous Lead

As shown in FIGS. 1 and 2, the percutaneous lead 400 can include a proximal end 402 located internal to the user and a distal end 404 located external to the user, with a portion

406 that traverses the skin. The proximal end 402 can be electrically connected to the controller assembly 200 and the distal end 404 can be removably coupled to an external power supply (not shown). A cap 410 can be used to protect the external physical structure of the distal end 404 and connector, as well as the exposed metal connections that can be coupled to the external power supply. In some embodiments, this cap can be designed to be fluid resistant (or fluid proof). In some embodiments, the cap can prevent moisture from seeping into the connector and reaching the metal connections. The cap can also to prevent any electrical conduction from any outside element with the metal connections. In some embodiments, the cap can be waterproof and fluid resistant. The cap structure can be made of a metallic or non-conducting material; in either case, the cap design will have insulation to prevent shorting of the metal connections or conduction of electricity between an external source and the metal connections. When connected to an external power supply, power sufficient for the normal operation of the hybrid system 10 and to charge the power storage device(s) 350 can be transferred through the percutaneous lead 400 by redundant power and ground lines. When the percutaneous lead is disconnected from an external power supply, power for the normal operation of the hybrid system 10 can be supplied by the internal rechargeable power storage device(s) 350.

The distal end 404 of the percutaneous lead 400 can be electrically coupled to an external power source. In these circumstances, the external power source can supply power for normal operation of the internal components of the hybrid system 10 (e.g., the pump assembly 100, the controller assembly 200, and the like) and to recharge the power storage device(s) 350. The external power source can be in the form of external batteries, an external power source plugged into a traditional wall socket such that it can convert AC electricity to DC electricity, and the like. For example, when the percutaneous lead 400 is coupled to an external power source that is plugged into a wall socket, the user is limited in the distance that he can travel. In these circumstances, the user may be limited to a single room, a single building, and the like. Furthermore, due to the connection of the percutaneous lead 400 to the external power source, the user may be limited from performing activities requiring a high degree of freedom of physical movement and/or that involve exposure to liquids, including but not limited to daily activities such as taking a bath, grocery shopping, physical and sporting activities like swimming, golf, tennis, etc., and household maintenance.

To increase a user's freedom of movement, the hybrid ventricular assist system 10 can be configured to be electrically coupled via the percutaneous lead 400 to a portable external power source, such as external batteries. For example, FIGS. 7 and 8 depict a portable system for carrying external batteries. When the percutaneous lead is connected to a portable external power source, the user can experience improved mobility, comfort, independence, and self-esteem when compared to being coupled to a power source plugged into a wall socket. For example, the user can wear a garment that is designed to contain rechargeable batteries such that the user is free to perform household chores, travel to the grocery store, go on a walk, etc. When coupled to external batteries worn as part of a garment, a user is not restricted by a cord plugged into a wall and is free to partake in many normal day-to-day activities, thus leading to increased independence and self-esteem. Additionally, since the external power source is worn with the user, the possibility of pulling on the percutaneous lead and damaging surrounding tissue is reduced, leading to a decreased possibility of infection and increased comfort.

To further increase a user's freedom of movement, the hybrid ventricular assist system 10 can be used for extended periods of time without the use of an external power supply. For example, when a user desires to have a greater freedom of movement and comfort, the user can disconnect the distal end 404 of the percutaneous lead 400 from an external power source, thus freeing him from the limitations imposed by such an external power source. While disconnected from the external power source, the internal power storage device(s) 350 can supply the power for the normal operation of the hybrid system 10 (e.g., the pump assembly 100, the controller assembly 200, and the like) for an extended period of time (e.g., greater then 30 minutes, greater than 1 hour, greater than 2 hours, greater than 3.5 hours, and the like, based on the size and capacity of the internal power storage device 350). While unplugged from all external power sources, the user experiences greater freedom to take part in physical and passive activities, such as swimming and bathing, that would otherwise be complicated by external cords, batteries, and the like.

When the percutaneous lead 400 is reconnected to an external power source, the external power source can be used to not only support normal operation of the hybrid system 10, but also to recharge the internal power storage device(s) 350. Using the percutaneous lead 400 to transfer energy from an external power source allows for a greater power transfer efficiency, and thus faster recharge rate, than a transcutaneous power transmission system. In some embodiments, the internal power storage device(s) can be advantageously recharged from a functionally depleted state to a fully recharged state in less than 30 minutes.

As previously referenced, a blood pump system can use a transcutaneous power system to wirelessly transfer power from an external power source to components implanted in a user. For example, power can be transmitted from the external source to the internal components by generating a magnetic field in the external coil and converting the magnetic field to electrical power in the internal coil, which is distributed to the other internal components. However, transcutaneous power systems can be limited in the rate of power transferred, for example, by the size of the coils. To increase the rate at which the power storage device(s) are charged, larger coils can be used. However, larger coils occupy additional internal space, which can result in an increased possibility of infection, and can result in the user carrying additional external equipment. Smaller coils, however, have slower transfer rates. Furthermore, transcutaneous power transmission can lose power during transmission, some of which is lost as heat within the tissues separating the internal and external transmission coils. This heating can be damaging to tissue. Additionally, due to energy lost during transmission, a user wearing external batteries, each with a fixed energy capacity, would have less time in between battery changes when using a transcutaneous power transfer system when compared to transferring power via the percutaneous lead 400. Also, fixation of the coils is critical for maintaining optimal alignment. As the coils become more decoupled (i.e. through misalignment and/or separation), efficiency of the transfer drops.

The percutaneous lead 400 can, in some embodiments, have a cross sectional area of less than about 0.10 square inches (e.g., a diameter that is less than about 0.3 inches). When using a reduced-diameter percutaneous lead 400, a smaller opening in the user's skin is used to accommodate the percutaneous lead 400. Reducing the diameter of the percutaneous lead that traverses the skin of the user has the beneficial effect of exposing less tissue, thus decreasing the possibility of infection around this opening. While a larger diameter percutaneous lead can increase transfer of both power and data to the internal components, a reduction in the diameter of the percutaneous lead can be achieved by using the percutaneous lead to only transfer power. The use of highly conductive materials in the percutaneous lead can be used to offset the smaller diameter, or the reduced cross-sectional capacity of the conductors. Accordingly, in some embodiments, control data is transmitted via wireless communication, thus allowing for a reduction in the diameter of the percutaneous lead 400. In comparison, exemplary percutaneous leads that include redundant sets of wires for transferring both power and data can have diameters that exceed 0.75 inches in diameter. In other embodiments, for example in ventricular assist systems lacking an internal controller device 210, a larger diameter percutaneous lead may be used to reliably transfer both power and data to the internal components. In these examples, the percutaneous lead can have a diameter that is greater than 0.5 square inches (e.g., greater than 0.75 inches in diameter).

Figure 4:
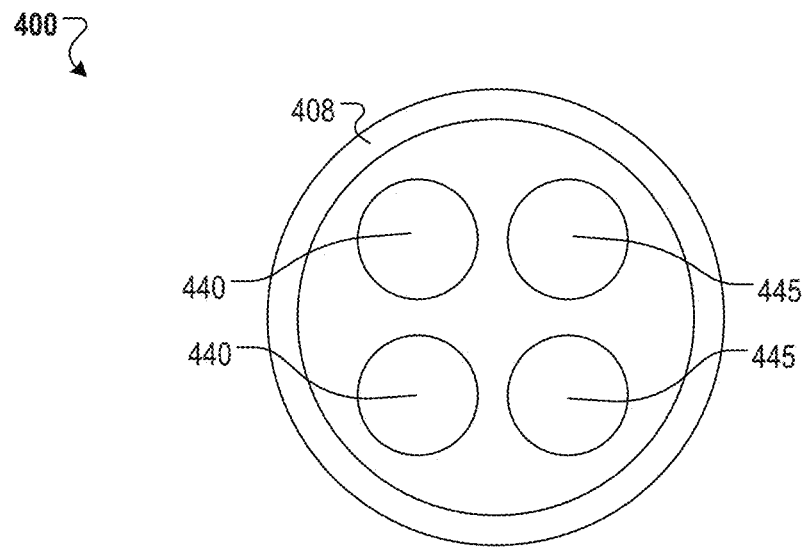
FIG. 4 is a cross-sectional view of one embodiment of a compact percutaneous lead with two sets of redundant power leads.

FIG. 4 is a cross-sectional view of a compact percutaneous lead 400 with two sets of redundant power leads. The percutaneous lead 400 can include a flexible outer housing 408 enclosing redundant electrical lead sets 440 and 445, for example as discussed in U.S. patent application Ser. No. 12/472,812, filed May 27, 2009, which is hereby incorporated by reference. In this configuration, electrical energy can be supplied from an external power source to the internal components of the hybrid ventricular assist system 10 (e.g., the blood pump 110, the controller device 210, the power storage device(s) 350, and the like). Each of the lead sets 440 and 445 can be capable of transferring all of the power for normal operation of the hybrid system 10, including recharging of the power storage device(s) 350, resulting in fully redundant energy transfer. Thus, if one of the conductors of one of sets 440 and 445 becomes damaged such that it is unable to transfer electrical energy, the system 10 can be fully powered by the one set 440 and 445 that remains intact. Furthermore, if one conductor of each set is damaged, power can be transferred by using non-damaged conductors from each set In examples where the percutaneous lead 400 contains only the lead sets 440 and 445 for transferring energy, the percutaneous lead 400 has a smaller cross-sectional area than in cases where additional wires are included for data transfer.

The cross-sectional area of the percutaneous lead 400 can be further decreased by, for example, including only a single set of power transfer wires. In other examples, the cross-sectional area of the percutaneous lead 400 may be decreased by decreasing the diameter of the lead sets 440 and 445 (e.g., by configuring them such that they are not fully redundant). In this example, each lead set 440 and 445 may be configured to carry only a percentage (e.g., less than 100%, 95%, 64%, 50%, and the like) of the total energy used during normal operation of the system 10 and recharging of the power storage device(s) 350. For example, each lead set 440 and 445 may be configured to supply sufficient power for normal operation of the hybrid system 10 and to trickle charge the power storage device(s) 350. In this example, when both lead sets 440 and 445 are functional, the hybrid system 10 can be supplied with power for normal operation and with sufficient power such that the power storage device(s) 350 can be quickly charged (e.g., the power storage devices can be recharged in less than 60 minutes). In other embodiments, the system can have a longer recharge time, depending on the type of power storage device and the percutaneous lead. However, if one of the lead sets 440 and 445 becomes non-functional (e.g., the lead set is damaged and becomes unable to transmit power), the system 10 can operate normally with the exception of charging the internal power storage device(s) 350, which will be accomplished at a slower rate. In this example, a redundancy is provided for normal operation of the system 10 while further reducing the diameter of the percutaneous lead 400, thus further decreasing the possibility of infection.

The hybrid ventricular assist system 10 can include other features that decrease the cross-sectional area of the percutaneous lead 400 while allowing for power and data transfer through the lead 400. For example, the lead 400 can include the lead sets 440 and 445 configured to transfer power from a power source external to a user to the internal components of the system 10. Power transferred from an external power source, for example, can be used for normal operation of the blood pump 110 and to recharge the internal power storage device(s) 350. Since power for the normal operation of the internal components of the system 10 can come from the power storage device(s) 350, power transfer can be temporarily discontinued through one or more of the lead sets 440 and 445, thus leaving one or more of the lead sets 440 and 445 available for the transfer of data. When the data transmission is complete, power once again can be transferred through the lead sets 440 and 445. This feature for the temporary cessation of power transfer can be incorporated into other percutaneous lead configurations, can be combined with other lead-size-reducing features, and is not restricted to the four-wire percutaneous lead depicted in FIG. 4. In some embodiments, the percutaneous lead includes two non-redundant sets of wires, one set for charging the power storage device(s) 350 and one set for providing power to the blood pump. In such an embodiments, a disabled recharging set can be rerouted to simply provide power to the blood pump.

Figure 6:
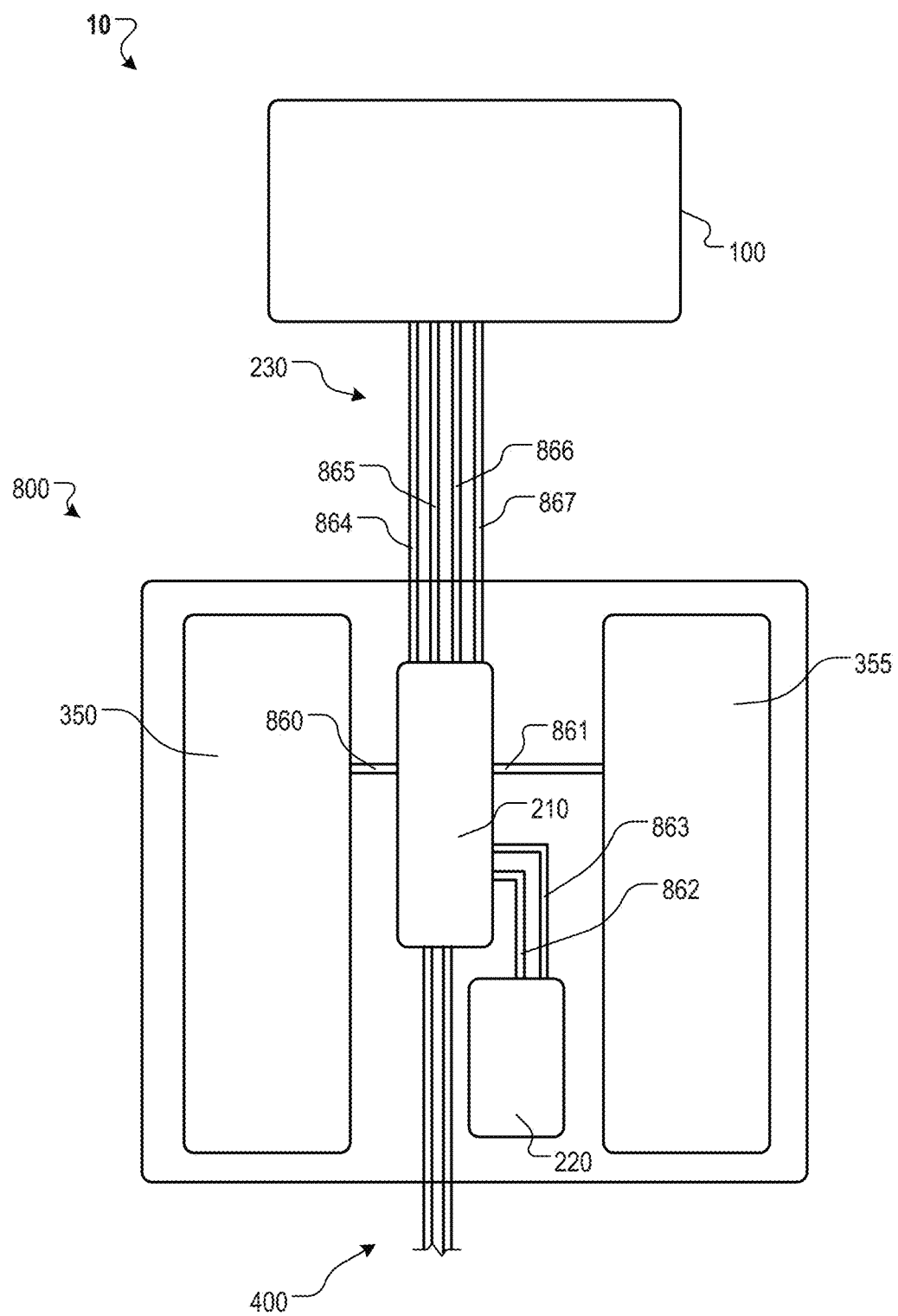
FIG. 6 is a schematic representation of one embodiment of a mobility-enhancing hybrid ventricular assist system including a blood pump, a controller, rechargeable power storage devices, and a compact percutaneous lead.

FIG. 6 is a schematic representation of the mobility-enhancing hybrid ventricular assist system 10 including the blood pump assembly 100, the controller assembly 200, the rechargeable power storage devices 350 and 355, and the compact percutaneous lead 400. The hybrid system 10 can be configured to reduce the diameter of the percutaneous lead 400. In some embodiments, the hybrid system 10 includes internal controller assembly 800 that can control functions of the hybrid system 10 and can wirelessly communicate with external components. Due at least in part to the presence of the internal controller assembly 800, data communication between the internal controller assembly 800 and external components can be transmitted in a manner other than through the percutaneous lead 400. Since the percutaneous lead 400 can be limited to the transfer of electrical energy, the resulting diameter of the percutaneous lead 400 can be smaller than if data transfer also took place through the percutaneous lead 400. For example, the controller device 210 can be electrically connected to the two power storage device(s) 350 and 355 with lead sets 860 and 861, respectively, and to the wireless telemetry device with redundant data lead sets 862 and 863. Furthermore, the controller device 210 can be electrically connected to the pump assembly with two redundant power lead sets 864 and 865 and two redundant data lead sets 866 and 867. In this example, the internal controller 210 is electrically connected to the pump assembly 100 by eight wires, but only four wires are used in the percutaneous lead 400. In examples where a controller device is external to the patient, additional wires may be used in the percutaneous lead that traverses the skin of the user.

The percutaneous lead 400 can additionally include other features that reduce a user's possibility of infection. As described above, an opening in the skin exposes tissue to infection. Additionally, movement of the portion 406 of the percutaneous lead 400 that traverses the skin opening in relation to the skin opening itself can cause damage to tissue surrounding the percutaneous lead 400, thus increasing the possibility of infection. The hybrid system 10 can be configured to include features that reduce movement of the internal portion of the percutaneous lead 400 relative to the user. For example, as depicted in FIGS. 1 and 2, the percutaneous lead 400 can include a strain-relief portion 420 for anchoring the percutaneous lead 400 to the user and for reducing the strain on the portion of the percutaneous lead exiting the user's body. In another example, the percutaneous lead 400 can include a low-force breakaway portion 430 that can separate when subjected to a pulling force that is less than the force expected to cause damage to the tissue surrounding the skin opening. Due to the presence of the internal power storage device, the percutaneous lead does not act as a lifeline, thus a breakaway connection can be used because an accidental disconnection will not result in a loss of power to the blood pump. When the distal end 404 of the percutaneous lead 400 is pulled with a force greater than the break-away force of the breakaway portion 430, the percutaneous lead 400 can reversibly separate into two portions, thus reducing the strain on the portion of the percutaneous lead 400 entering the skin opening. The two portions can be re-joined at the breakaway portion 430 when the stress on the breakaway portion 430 falls below the break-away force. While the percutaneous lead 400 is separated into the two portions, sufficient power to maintain normal operation of the hybrid system 10 can be supplied by the internal power storage device(s) 350. When the percutaneous lead 400 is reconnected, power to maintain normal operation of the hybrid system 10 can once again be supplied by the connected external power source, while also recharging the internal power storage device(s) 350.

The percutaneous lead can be connected to the external power source by use of a connector. For example, the connector can be flat, square, round, or any other shape. The connector can provide a fluid resistant or fluid proof connection. In some embodiments, the connector can prevent liquid water proof and water vapor proof.

Controller

The blood pump can be controlled by internal control circuitry. In some embodiments, the control circuitry can be a part of the blood pump assembly 100. In other embodiments, the control circuitry (e.g., controller device 210) can be within the same housing containing the rechargeable power storage device(s) 350, as depicted in FIGS. 1, 2, and 3B. In other embodiments, control circuitry can be within a dedicated implantable housing separate from both the blood pump assembly 100 and the housing containing the rechargeable power storage device(s) 350, as depicted in FIGS. 3A, 7, and 8. Internal control circuitry (e.g., the controller device 210) can in some embodiments communicate with an external controller and/or an external input device.

The internal control circuitry can include, but is not limited to, one or more features to monitor the operation of the hybrid ventricular assist system 10, to monitor the user (e.g., to detect blood pressure), to control predetermined functions of the hybrid system 10 (e.g., to control how power is supplied to the blood pump), and to inform the user of particular information regarding operation of the hybrid system 10 (e.g., by vibrating or by sending a signal to an external device). The internal control circuitry can include features for controlling the speed of the pump 110. In another example, the internal control circuitry can monitor functions of the system 10, such as the electrical charge level of (i.e. usable energy remaining in) the power storage device(s) 350. In still another example, the internal control circuitry can inform the user of alerts and alarms pertaining to the operation of the hybrid system 10, such as alerting the user when the charge level of one or more of the power storage devices 350 has fallen below a predetermined threshold, or signaling an alarm when a malfunction in the system 10 has occurred. The internal control circuitry can inform the user of a condition, for example, by initiating an internal vibrator, signaling a remote controller via the wireless telemetry unit 220, causing a light to flash, and the like. For example, in some embodiments, an external portion of the percutaneous lead 400 (e.g., the cap 410, the distal end 404 of the percutaneous lead 400, and the like) can include a light that can flash. For example, if the amount of power remaining in the internal power supply falls below a threshold and power is not being supplied to the system through the percutaneous lead, the controller can direct power though wires provided in the percutaneous lead 400 to a light in an external portion of the percutaneous lead or in the cap. In yet another example, the controller can monitor the inlet and outlet pressures of the pump 110, determine blood flow through the pump assembly 100, determine an activity level of the user and thereby change the speed of the pump, and the like. These controller functions can also be preformed using an external controller that communicates with the internal controller, for example using an external communication device that performs wireless 2-way communication. The controller can also detect whether power is being provided through the percutaneous lead and to control whether that power is used to simply operate the blood pump or to also recharge the internal power supply. The internal controller can also include electrical circuitry to detect and shut down (if necessary) failed conductors in the percutaneous lead and/or between the controller and blood pump or other internal housings. This can be accomplished by detecting increased or decreased electrical resistance. In some embodiments, the controller can then use a redundant conductor. The controller can also provide different alarms depending on whether power is being supplied via the percutaneous lead, and in some embodiments depending on which external power source is active (e.g., external portable battery versus converted AC power source). Internal alarms can include internal vibrators (e.g., piezoelectric buzzers). External alarms can include lights and/or audible alarms.

The controller can also include a memory buffer to store information. The member buffer can store acquired data, such as pump speed and physiological data of the patient (e.g., blood pressure). The member buffer can also be used to record information about how the pump system is operating, including error information and/or battery life. The information in the memory buffer can be downloaded to an external system via the percutaneous lead and/or via a telemetry system. The memory buffer can provide a means to record information when the user is disconnected and/or away from external components.

External Components

The hybrid ventricular assist system 10 can be electrically coupled via the percutaneous lead 400 to an external power source that can supply power for normal operation of the hybrid system 10. The external power source can be external batteries, a wall socket, or the like. An external power source can have different levels of technological complexity, ranging from a simple AC transformer/adapter to a control console that is used to diagnose, control, and/or modify functions of the pump. In some embodiments, the external batteries can be part of or connected to an external controller, as depicted in FIG. 7. In other embodiments, such as depicted in FIG. 8, the percutaneous lead 400 can be directly connected to external batteries. Power supplied by the external power source can be used to recharge the power storage device(s) 350. As noted above, the hybrid system 10 can also include an external controller (e.g., an external controller 500) that can be used in conjunction with or in lieu of the internal controller device 210.

Referring again to FIG. 1, the hybrid ventricular assist system 10 can include the external monitoring device 500 in wireless communication with the internal components of the hybrid system 10 (e.g., the controller device 210, the wireless telemetry device 220, the pump assembly 100, and the like). The external controller 500 can include the programming wand 510. The programming wand can include the built-in display 512 for displaying menus, data, and the like, the external wireless telemetry device 514 for communicating with the internal telemetry device 220, and the one or more user-selectable buttons 516 (e.g., four buttons in this embodiment) for navigating menus, selecting features, inputting data, and the like.

The external electrical interface can include electronics to detect and shut down (if necessary) any faulty conductors in the percutaneous cable.

Schematics

FIG. 3A is schematic representation of one embodiment of the mobility-enhancing hybrid ventricular assist system 10 including a controller assembly 600 and a separate power storage assembly 300. As depicted in FIG. 3A, the hybrid system 10 also includes the internal blood pump assembly 100, one or more rechargeable storage devices (e.g., the power storage device 350, and the like) included in the power storage assembly 300, and the compact percutaneous lead 400. The controller assembly 600 can be implanted in, for example, the thorax, the abdomen, or other parts of a patient and can be electrically connected to the pump assembly 100 via the electrical conduit 230 such that the controller assembly 600 can control functions of and monitor the pump assembly 100. The controller assembly 600 can be connected to the power storage assembly 300 via an electrical conduit 330 and can control charging of the power source contained within the power storage assembly 300. Power for normal operation of the hybrid system 10 can be supplied by the power storage assembly 300. The power storage device 350, for example, can be directly electrically connected to the controller assembly 600, the pump assembly 100, and the like, and can be implanted in the thorax, the abdomen, or other parts of the user in a location separate from those of the controller assembly 600 and the pump assembly 100. In other embodiments, the power storage device 350 may indirectly provide power to the pump assembly 100. Power storage devices, in addition to or in lieu of the power storage device 350, can be included in one or both of the blood pump assembly 100 and the controller assembly 600.

FIG. 3B is a schematic representation of certain embodiments of the mobility-enhancing hybrid ventricular assist system 10 connected to an external power source 20. The hybrid system 10 can include features that allow for power to and control of an internal pump without constant connection to external devices. For example, the hybrid system 10 can include the internal controller assembly 200 that includes the controller device 210, the wireless telemetry device 220, and the two rechargeable power storage devices 350 and 355. The controller assembly 200 can be implanted in a single location (e.g., in the thorax, the abdomen, and the like) with the electrical conduit 230 electrically connecting elements contained within the controller assembly 200 (e.g., the controller device 210, the wireless telemetry device 220, the rechargeable power storage devices 350 and 355, and the like) to the pump assembly 100. The electrical conduit 230 can be removably coupled to the controller assembly 200 via the bulkhead connector 202 and to the pump assembly via the bulkhead connector 102. The percutaneous lead 400 can be coupled to the controller assembly 200 via a bulkhead connector 204. In some embodiments, the electrical conduit 230 has a larger diameter than the percutaneous lead 400, as the electrical conduit 230 includes wires for both the transmission of power and data between the controller assembly 200 and the pump assembly 100.

The controller assembly 200 can include the power storage device 350 and the optional power storage device 355 that are substantially equivalent and that can each supply electrical energy to the individual components of the hybrid ventricular assist system 10 (e.g., the controller device 210, the wireless telemetry device 220, the pump assembly 100, and the like). In some examples, the power storage devices 350 and 355 can include one or more direct electrical connections to the pump assembly 100, while in other examples energy can be transferred to the pump assembly 100 via the controller device 210. Similarly, energy can be transferred to other components of the hybrid system 10 (e.g., the wireless telemetry device 220 and the like) either directly, or through intervening components. The hybrid system 10 can be configured such that each of the power storage devices 350 and 355 is a redundant source of energy for all components of the system 10, thus the system 10 can function normally even when only one of the power storage devices 350 and 355 is supplying energy to the hybrid system 10. Power can also be supplied for normal operation of the hybrid system 10 by an external power source (e.g., the external power source 20) when connected to the percutaneous lead 400. When connected in this manner the internal power storage devices 350 and 355 can be charged by the external power source 20.

Figure 5:
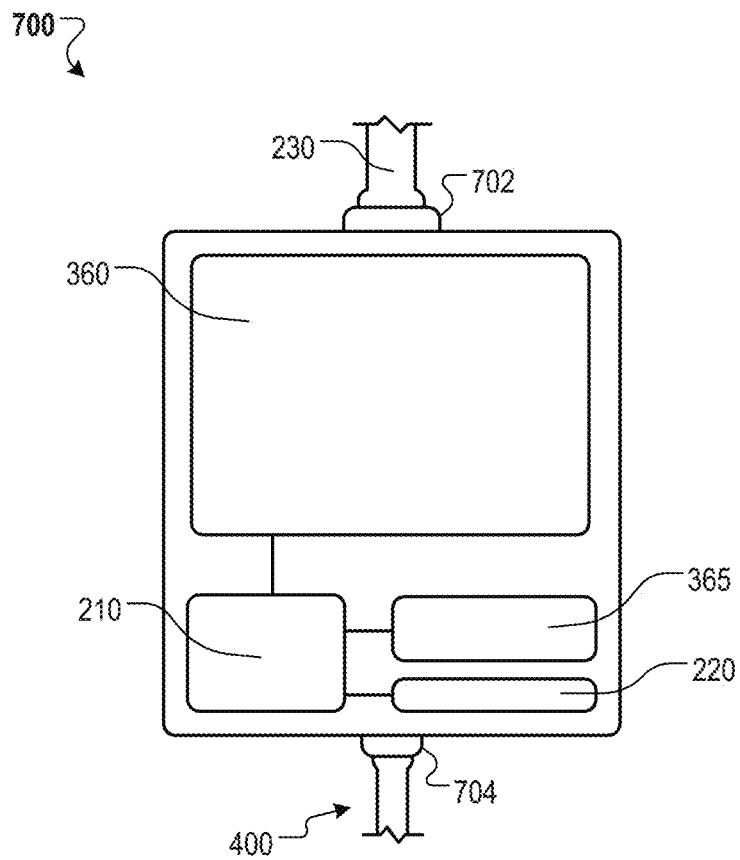
FIG. 5 is a schematic representation of one embodiment of an implantable controller with two unequal capacity rechargeable storage devices.

FIG. 5 is a schematic representation of an implantable controller assembly 700 with two unequal capacity rechargeable storage devices. The hybrid ventricular assist system 10 can include the internal controller assembly 700 that includes the controller device 210, the wireless telemetry device 220, and rechargeable power storage devices 360 and 365. In these embodiments, the controller assembly 700 (including the internal power storage devices 360 and 365) can be implanted in a single location (e.g., in the thorax, the abdomen, and the like) with the electrical conduit 230 electrically connecting elements contained within the controller assembly 700 (e.g., the controller device 210, the wireless telemetry device 220, the rechargeable power storage devices 360 and 365, and the like) to the pump assembly 100. The electrical conduit 230 can be removably coupled to the controller assembly 700 via a bulkhead connector 702 and the percutaneous lead 400 can be coupled to the controller assembly 700 via a bulkhead connector 704.

The controller assembly 700 can include the power storage devices 360 and 365 that can supply electrical energy to the individual components of the hybrid ventricular assist system 10 (e.g., the controller device 210, the wireless telemetry device 220, the pump assembly 100, and the like) and that do not have substantially equivalent electrical energy capacities. As with previously described embodiments, the hybrid system 10 can include one or more direct electrical connections from the internal power storage devices (e.g., the devices 350, 355, 360, 365, and the like) to the pump assembly 100 (see FIG. 2). In other examples, energy can be transferred from the internal power storage devices to the pump assembly 100 via the controller device 210. Similarly, energy can be transferred to other components of the hybrid system 10 (e.g., the wireless telemetry device 220 and the like) either directly, or indirectly through intervening components. The hybrid system 10 can be configured such that each of the power storage devices 360 and 365 is a redundant source of power for normal operation of the system 10, thus the system 10 can function normally even when only one of the power storage devices 360 and 365 is supplying power to the hybrid system 10. However the power storage devices 360 and 365 can be configured to store different amounts of energy. For example, the power storage device 360 can be configured with a larger capacity than the power storage device 365. When the system 10 is disconnected from an external source, initial power can be supplied by the power storage device 360 and the power storage device 360 can be configured to power the system 10 for a period of time greater than 30 minutes. When the power storage device 360 is no longer able to supply sufficient power to normally operate the system 10, the controller device 210 can notify the user (e.g., by initiating a vibrating alarm, causing the cap 410 to illuminate, sending a signal to an external controller, and the like) that the power storage device 360 has been depleted and the system 10 is operating using power supplied from power storage device 365. The power storage device 365 can be configured to supply the power for normal operation of the system 10, for example, for a period of 10 minutes, to allow a user to reconnect the system 10 to an external power supply.

Referring now to FIG. 6, the hybrid ventricular assist system 10 can be configured to reduce the diameter of the percutaneous lead 400. In some embodiments, the hybrid system 10 includes internal controller assembly 800 that can control functions of the hybrid system 10 and can wirelessly communicate with external components. Due at least in part to the presence of the internal controller assembly 800, data communication between the internal controller assembly 800 and external components can be transmitted in a manner other than through the percutaneous lead 400. Since the percutaneous lead 400 can be limited to the transfer of electrical energy, the resulting diameter of the percutaneous lead 400 can be smaller than if data transfer also took place through the percutaneous lead 400. For example, the controller device 210 can be electrically connected to the power storage device 350 and the optional power storage device 355 with lead sets 860 and 861, respectively, and to the wireless telemetry device 220 with redundant data lead sets 862 and 863. Furthermore, the controller device 210 can be electrically connected to the pump assembly with two redundant power lead sets 864 and 865 and two redundant data lead sets 866 and 867. In this example, the internal controller 210 is electrically connected to the pump assembly 100 by eight wires, but only four wires are used in the percutaneous lead 400. In examples where a controller device is external to the patient, additional wires may be used in the percutaneous lead that traverses the skin of the user.

Additional Configurations

FIG. 7 is a front view depicting an embodiment of the hybrid ventricular assist system 10 coupled to a portable external controller 30 and two external batteries 40. In the embodiment depicted here, the hybrid system 10 includes the internal blood pump assembly 100 (including a centrifugal blood pump 150), an internal controller assembly 900, the internal rechargeable power storage assembly 300, including one or more rechargeable storage devices (e.g., the devices 350, 360, 365, and the like), and the compact percutaneous lead 400. The controller assembly 900 can be implanted in, for example, the thorax, the abdomen, or other part of a patient, and can be electrically connected to the blood pump 150 such that the controller assembly 900 can control functions of and monitor the pump assembly 100 and control charging of the power sources contained within the power storage assembly 300. Power for normal operation of the hybrid system 10 can be supplied by the power storage assembly 300. The power storage assembly 300 can, for example, be electrically connected to the controller assembly 900, the pump assembly 100, and the like, and can be implanted in the thorax, the abdomen, or another part of the user in a location separate from those of the controller assembly 900 and the pump assembly 100. This can allow for outpatient replacement of the power storage device if necessary.

As described previously, the hybrid ventricular assist system 10 can be electrically coupled via the percutaneous lead 400 to an external controller and power source. However, when coupled to a non-portable power source (e.g., a power source plugged into a conventional wall socket) a user's independence, mobility, and comfort can be limited. To increase the user's mobility, the percutaneous lead 400 can be uncoupled from the non-portable external controller and power source (not shown) and coupled to the portable external controller 30 and the two external batteries 40. When coupled to the external controller 30 and the two external batteries 40, the power for normal operation of the blood pump 150 can be supplied by the external batteries 40, thus not decreasing the energy level contained within the internal power storage assembly 300. Furthermore, power supplied by the external batteries 40 can be used to recharge the power storage assembly 300. For example, the user can wear a garment, such as a holster vest 50 that can include battery holders 52 such that the weight of the external batteries 40 can be substantially supported by the shoulders of the user. A waist belt 54 can be included with the holster vest 50 to firmly hold the battery holders 52 (including the coupled batteries 40) and the external controller 30 firmly against the user. With the distal end 404 of the percutaneous lead 400 coupled to the external controller 30, the user is able to move around untethered, for example, by an external power source plugged into a wall socket.

When the percutaneous 400 lead is connected to a portable external power source such as the external batteries 40, the user can experience improved mobility, comfort, independence, and self-esteem when compared to being coupled to a power source plugged into a wall socket. For example, the user can wear a garment (e.g., the holster vest 50, a carrying case, and the like) that is designed to contain the rechargeable batteries 40 such that the user is free to perform household chores, travel to the grocery store, go on a walk, etc. When coupled to the external batteries 40 worn as part of a garment, a user is not restricted by a cord plugged into a wall and is free to partake in many normal day-to-day activities, thus leading to increased independence and self-esteem. Additionally, since the external power source is worn with the user, the possibility of pulling on the percutaneous lead 400 and damaging surrounding tissue is reduced, leading to decreased possibility of infection and increased comfort.

For an even greater degree of mobility, the user can uncouple the percutaneous lead 400 from the external controller 40. In some circumstances, a user may be restricted from performing certain activities while wearing a garment containing electronic devices. For example, certain forms of physical exercise, such as swimming, would be difficult while wearing a garment containing electronic devices. Furthermore, while being coupled to an external power supply, even a portable one such as batteries included in a garment, could be an impedance and inconvenience for activities such as gardening, a brisk walk, a short game of tennis or golf, etc. As such, a user can uncouple the percutaneous lead 400 from all external devices, remove the external devices (e.g., the holster vest 50, the battery holsters 52, the belt 54, the external controller 30, the external batteries 40, and the like) for an extended period of time for performing activities that might otherwise not be possible. Being connected to an external power source, even a portable battery, can also complicate certain relatively passive activities, such as taking a bath, that include exposure to liquids.

FIG. 8 is a front view depicting another embodiment of the hybrid ventricular assist system 10 coupled to two external batteries 40. Similar to the embodiment described in connection with FIG. 7, the hybrid system 10 can include the internal blood pump assembly 100 (including the centrifugal blood pump 150), an internal controller assembly 1000, the internal rechargeable power storage assembly 300 (e.g., not contained within the controller assembly 1000), and the compact percutaneous lead 400. In the embodiment described here, however, the hybrid ventricular assist system 10 can be free of an external wired controller (such as the controller 30 depicted in FIG. 7). In these embodiments, an adapter 44 can be coupled to the distal end 404 percutaneous lead 400 such that the electrical conduits 41 coupled to each of the external batteries 40 can be electrically connected to the percutaneous lead 400 (e.g., by coupling the ends 42 of the electrical conduits 41 to the adapter 44) without the use of an external controller 30. Additionally, an external device (e.g., a PDA 530) can be in wireless communication with the internal controller assembly 1000 for the purpose of relaying data to the user, indicating to the user the presence of alerts and alarms, and allowing the user to program certain features of the hybrid system 10. As with the embodiment described in connection with FIG. 7, the user can attain a greater degree of mobility by removing the external components to perform activities that might otherwise not be possible.

Implantation Procedure

Referring again to FIGS. 1-2, prior to implantation, the connectors of the pump assembly 100 (e.g., connector 102) and the controller assembly 200 (e.g., connectors 202 and 204) can be capped to protect the connectors from contaminants. In some embodiments, a pocket is developed between the posterior sheath and the rectus muscle to accommodate the controller assembly 200. A tunneling device can be utilized to create tunnels between the internal components (e.g., the pump assembly 100 and the controller assembly 200) for the passage of intervening conduits (e.g., the electrical conduit 230) and to create a tunnel between the pocket to contain the controller assembly 200 and the exit location of the percutaneous lead 400. The electrical conduit 230 can be inserted in the tunnel leading to the blood pump assembly 100 and secured to the bulkhead connector 102. The percutaneous lead 400 can be tunneled to the pocket developed for the controller assembly 200, the controller assembly 200 can be positioned in the pocket, the conduit 230 can be secured to the controller assembly 200 using the bulkhead connector 202, and the percutaneous lead can be secured to the bulkhead connector 204 in the controller assembly 200. Pumping may be subsequently initiated (e.g., by placing the telemetry wand 510 over the controller assembly 200 and initiating a start-up mode) using power transferred through the percutaneous lead 400. The optional display 520 can display information such as hemodynamic parameters. After verifying proper functioning of the hybrid system 10, the internal power storage device(s) 350 can then be enabled and tested. After completion of the operative procedure, chest and abdominal radiographs can be obtained to confirm component positioning.

Other Embodiments

While several configurations of the hybrid ventricular assist system 10 have been described here, it should be understood that there are many combinations of pump assemblies, controller assemblies, power storage assemblies, power storage devices, external controllers, external power sources, and external communication devices that can be employed to perform the functions of the system 10 described above. Nevertheless, it will be understood that various modifications may be made without departing from the spirit and scope of this disclosure. For example, the hybrid system 10 can include a controller assembly (e.g., the controller assembly 200, 700, and the like) and a power storage assembly 300 that both include rechargeable power storage devices (e.g., the devices 350, 360, 365, and the like). In another example, the pump assembly 100 can include the controller circuitry (e.g., the controller device 210, the wireless telemetry device 220, and the like) used to control and monitor the function of the pump 110. As such, such hybrid ventricular assist systems can be free of a separate controller assembly (such as the controller assembly 200, 700, and the like). Furthermore, there are many devices that can be used as an external communication/controller device. For example, the hybrid system 10 can wirelessly communicate with cell phones, PDAs, laptop computers, tablet computers, desktop computers, and the like that include the capability for wireless communication. Accordingly, other embodiments are within the scope of the following claims.

What is claimed is:

1. A method for controlling an implantable blood pump with an implantable internal controller, the method comprising:

determining a power level of at least one implantable rechargeable battery;

adjusting a recharge of the at least one implantable rechargeable battery based on the determined power level;

receiving pump information from the implantable blood pump, the pump information associated with an operational speed of the implantable blood pump;

transmitting the pump information to an external controller;

receiving, by the implantable internal controller, commands from the external controller to change the operational speed of the implantable blood pump based on the transmitted pump information; and adjusting, by the implantable internal controller, power delivery to the implantable blood pump from an external power source or the at least one rechargeable battery in response to the commands to change the operational speed of the implantable blood pump;

wherein the implantable internal controller is physically separated from the implantable blood pump and implanted at a location removed from the implantable blood pump.

2. The method of claim 1, wherein the external controller comprises a monitoring device, and wherein the commands from the external controller comprise commands from the monitoring device via a percutaneous cable, and wherein the pump information is transmitted to the external controller via the percutaneous cable.

3. The method of claim 1, wherein the external controller comprises a programming wand coupled with a monitoring device, and wherein the commands from the external controller comprise commands from the programming wand via a telemetry device, and wherein the pump information is transmitted to the external controller via the telemetry device.

4. The method of claim 1, wherein power is delivered to the implantable blood pump via an electrical conduit, and wherein the pump information comprises an inlet pressure of the implantable blood pump or an outlet pressure of the implantable blood pump.

5. The method of claim 1, further comprising determining a blood flow through the implantable blood pump and adjusting power to the implantable blood pump to adjust the operational speed of the implantable blood pump per the determined blood flow.

6. The method of claim 1, further comprising determining an activity level of a patient and adjusting power to the implantable blood pump to adjust the operational speed of the implantable blood pump per the determined activity level of the patient.

7. The method of claim 1, further comprising transmitting battery information associated with the implantable rechargeable battery to the external controller, the battery information comprising battery life information.

8. The method of claim 7, further comprising triggering an alert to a patient when the battery information indicates a battery level below a low power threshold.

9. The method of claim 8, further comprising terminating power transmission from the at least one implantable rechargeable battery to the implantable blood pump when the battery information indicates a battery level below a damage threshold, the damage threshold being lower than the low power threshold.

10. The method of claim 1, further comprising transmitting error information to the external controller comprising at least one of: battery error information, electrical conduit error information, or percutaneous cable error information, wherein:

the electrical conduit error information or the percutaneous cable error information comprises failed conductor information associated with an electrical conduit or a percutaneous cable.

11. The method of claim 1, further comprising storing internal system information to a memory buffer coupled with the implantable internal controller, the stored internal system information comprising at least one of pump speed information, physiological data of a patient, error information, or battery life information for subsequent download via a telemetry system or a percutaneous cable.

12. The method of claim 1, wherein the implantable internal controller is implanted within an abdomen of a patient.

13. The method of claim 1, wherein the implantable rechargeable battery is implanted within an abdomen of a patient.

14. The method of claim 1, further comprising monitoring for one or more failed electrical conductors in a percutaneous cable coupled to the external controller or an electrical conduit coupled to the implantable blood pump.

15. The method of claim 14, further comprising shutting down the one or more failed electrical conductors.

16. The method of claim 14, further comprising switching from a failed electrical conductor to a redundant conductor.

17. The method of claim 14, wherein monitoring for failed electrical conductors comprises detecting changes in electrical resistance.

18. A method for controlling an implantable blood pump with an implantable internal controller, the method comprising:

monitoring a charge level of at least one implantable rechargeable battery;

adjusting a recharge of the at least one implantable rechargeable battery based on the charge level;

alerting a patient when the charge level falls below a pre-determined threshold;

receiving pump information from the implantable blood pump, the pump information associated with an operational speed of the implantable blood pump;

transmitting the pump information to an external controller;

receiving commands from the external controller to change the operational speed of the implantable blood pump; and adjusting power delivery to the implantable blood pump from an external power source or the at least one rechargeable battery in response to the commands to change the operational speed of the implantable blood pump;

wherein the implantable internal controller is physically separated from the implantable blood pump and implanted at a location removed from the implantable blood pump.

19. The method of claim 18, wherein the external controller comprises a monitoring device, and wherein the commands from the external controller comprise commands from the monitoring device via a percutaneous cable, and wherein the pump information is transmitted to the external controller via the percutaneous cable.

20. The method of claim 18, wherein the external controller comprises a programming wand coupled with a monitoring device, and wherein the commands from the external controller comprise commands from the programming wand via a telemetry device, and wherein the pump information is transmitted to the external controller via the telemetry device.

* * * * *